US006831204B2

(12) United States Patent
Chen et al.

(10) Patent No.: US 6,831,204 B2
(45) Date of Patent: Dec. 14, 2004

(54) MCRALY SUPPORTED CATALYSTS FOR OXIDATIVE DEHYDROGENATION OF ALKANES

(75) Inventors: Zhen Chen, Ponca City, OK (US); Sriram Ramani, Ponca City, OK (US); Lisa M. Carmichael, Ponca City, OK (US); Joe D. Allison, Ponca City, OK (US)

(73) Assignee: ConocoPhillips Company, Houston, TX (US)

( * ) Notice: Subject to any disclaimer, the term of this patent is extended or adjusted under 35 U.S.C. 154(b) by 0 days.

(21) Appl. No.: 10/269,174

(22) Filed: Oct. 11, 2002

(65) Prior Publication Data

US 2004/0072685 A1 Apr. 15, 2004

(51) Int. Cl.[7] .......................... C07C 5/327; C07C 5/333
(52) U.S. Cl. ...................... 585/656; 585/658; 585/660; 585/661; 585/662; 585/663
(58) Field of Search ................. 585/656, 658, 585/660, 661, 662, 663

(56) References Cited

U.S. PATENT DOCUMENTS

| | | | |
|---|---|---|---|
| 4,299,192 A | 11/1981 | Enga | 122/4 |
| 4,532,191 A | 7/1985 | Humphries et al. | 428/678 |
| 5,511,972 A | 4/1996 | Dalla Betta et al. | 431/170 |
| 5,639,401 A | 6/1997 | Jacobs et al. | 252/373 |
| 6,042,883 A | 3/2000 | Paul et al. | 427/226 |
| 6,410,159 B1 | 6/2002 | Hermanck | 428/570 |
| 6,475,647 B1 | 11/2002 | Mendez Acevedo et al. | 428/678 |

OTHER PUBLICATIONS

Czech et al., *Influence of the Surface Roughness on the Oxide Scale Formation on McrAlY coatings Studied in Situ by High Temperature X-ray Diffraction*, Surface and Coatings Technology 108–109 (1998) pp. 36–42, no month.

Herman, *Return to the Planet Snecnak All About 'Emerawleer'*, Praxair Surface Technologies, Oct. 26, 1999, pp. 1–3, no month.

*Primary Examiner*—Elizabeth D. Wood
(74) *Attorney, Agent, or Firm*—Conley Rose, P.C.

(57) ABSTRACT

A new family of oxidative dehydrogenation catalysts having MCrAlY supports can be used in the production of olefins. Olefins are produced by heating a feed stream comprising at least an alkane and an oxidant to a temperature between 25° C. and 800° C.; contacting the feed stream with a catalyst comprising an MCrAlY structure and, optionally, a Group VIII promoter metal coating, wherein M is a base metal, or combination of base metals; and maintaining a contact time of the alkane with the catalyst of less than 200 milliseconds under conditions sufficient to achieve oxidative dehydrogenation of the alkane. M may comprise a metal selected from the group consisting of Group IB–VIIB metals, Group IIIA–VA metals, lanthanide metals, iron, cobalt, nickel, and combinations thereof. More particularly, M may comprise a metal selected from the group consisting Tb, Sm, Pr, Fe, Ni, Co, and combinations thereof.

21 Claims, No Drawings

MCRALY SUPPORTED CATALYSTS FOR OXIDATIVE DEHYDROGENATION OF ALKANES

FIELD OF THE INVENTION

This invention relates to high temperature, oxidation-resistant, aluminum containing oxide-dispersion-strengthened (ODS) alloy-supported catalyst compositions for oxidative dehydrogenation processes and a method of using such catalysts in the presence of hydrocarbons. More particularly, this invention relates to compositions of MCrAlY-supported catalysts for the production of olefins by oxidative dehydrogenation of hydrocarbons in short-contact time reactors (SCTRs).

BACKGROUND OF THE INVENTION

Dehydrogenation of hydrocarbons is an important commercial process. Dehydrogenation is the process used to convert aliphatics to olefins, mono-olefins to di-olefins, cycloalkanes to aromatics, alcohols to aldehydes and ketones, aliphatics and olefins to oxygenates, etc., by chemically removing hydrogen from the starting molecule(s). In more practical terms, this process has been used to produce commercially many of the precursors of products such as detergents, gasolines, pharmaceuticals, plastics, polymers, synthetic rubbers and many others. For example, polyethylene is made from ethylene, which is made from the dehydrogenation of ethane (i.e. aliphatic to olefin). More ethylene is produced in the U.S. than any other organic chemical. Thus, it is easy to appreciate the significance of the dehydrogenation process to industry.

Traditionally, the dehydrogenation of hydrocarbons has been carried out using steam cracking or non-oxidative dehydrogenation processes. Thermal or steam cracking is an extremely energy intensive process that requires temperatures in excess of 800° C. About $1.4 \times 10^{15}$ BTU's (equivalent to burning 1.6 trillion ft$^3$ of natural gas) are consumed annually to produce ethylene. In addition, much of the reactant (ethane) is lost as coke deposition. Non-oxidative dehydrogenation is dehydrogenation whereby no molecular oxygen is added.

Oxidative dehydrogenation of hydrocarbons (ODH) with short contact time reactors is an alternative to traditional steam cracking and non-oxidative dehydrogenation processes. During an ODH reaction, an oxidant is co-fed with saturated hydrocarbons. Typically the oxidant is a gas containing oxygen. The oxygen-containing gas may be pure molecular oxygen, air, oxygen-enriched air, oxygen mixed with a diluent, and so forth. However the presence of a diluent such as an inert gas in the oxidant increases the reactor and equipment size. The oxidant in the desired amount may be added in the feed to the dehydrogenation zone and the oxidant may also be added in increments to the dehydrogenation zone. Gas hourly space velocity (GHSV) is typically from 20,000 to 10,000,000 hr$^{-1}$. For the present process, GHSV is defined by the ratio of the volumetric flow rate (m$^3$/hr) of gaseous feed at normal pressure and temperature over the catalyst bed volume (m$^3$). The contact time of the reactants with the catalyst is typically in the 10–200 ms range. The reaction pressure is typically between 1 and 50 bars.

The capital costs for olefin production via ODH are significantly less than with the traditional processes, because ODH uses simple fixed bed reactor designs and high volume throughput. In addition, ODH is an autothermal process, which requires no or very little energy to sustain the reaction. Energy savings over traditional, endothermic processes can be significant if the heat produced with ODH is recaptured and recycled. Often, the trade-off for saving money in commercial processes is loss of yield or selectivity; however, the ODH reactions are comparable to steam cracking in olefin selectivity and alkane conversion.

As mentioned above, ODH is an exothermic reaction, and temperatures at typical reaction conditions in excess of 1,000° C. may be required for successful operation. It is known that ceramic monolith catalyst supports are susceptible to thermal shock; that is, either rapid changes in temperature with time or substantial thermal gradients across the catalyst structure. Catalysts and catalyst supports for use in such a process must therefore be very robust, and avoid structural and chemical breakdown under the relatively extreme conditions prevailing in the reaction zone.

U.S. Pat. No. 5,639,401 discloses a porous monolithic foam catalyst support of relatively high tortuosity and porosity, preferably comprising at least 90 wt % zirconia for thermal shock resistance.

Complete oxidation of hydrocarbons, such as occur in automobile catalytic converters, also require catalysts, which function at high space velocities and also are stable at elevated temperatures of greater than about 700° C. U.S. Pat. No. 5,511,972 discloses a catalyst structure that is effective under the severe conditions encountered in automobile catalytic converters. The catalyst structure comprises a ferrous alloy as the catalyst support. The ferrous alloy contains aluminum, which forms micro-crystals or whiskers of alpha-alumina on the alloy surface when heated in air. A washcoat of gamma-alumina is added to the alpha-alumina surface followed by the deposition of palladium.

Materials such as oxide-dispersion-strengthened (ODS) alloys can withstand high temperatures (>700° C.) similar to those used in the ODH reaction system. As an example of ODS alloys, MCrAlY alloys have been used as a thermal coating or thermal barrier in high-temperature or corrosive environments such as diesel exhaust systems or gas turbine engines. As disclosed by Czech, et al., in *Surface and Coatings Technology*, 108–109 (1998) p. 36–42, stationary gas turbine engines for electric power generation operate at gas inlet temperatures that are as high as those in the ODH reaction zone. The turbine blades are subjected to very high thermal and mechanical loads and are additionally attacked by oxidation. To deal with the mechanical loads, the base material of the turbine blades is metallic in composition. To deal with the thermal and chemical stresses, the turbine blades have a coating with an MCrAlY composition, where M comprises Ni and/or Co, as a protective overlay coating against oxidation. Additional coatings may be added as thermal barriers. The overlay coatings are typically applied by either Low Pressure Plasma Spray or Vacuum Plasma Spray. The base material is protected in operation by an alumina scale, which forms from the overlay coating.

A MCrAlY alloy is comprised of chromium, alumina, yttrium and another metal or metal alloy M, with the metal preferably selected from the group of Ni, Co, Fe. The aluminum in MCrAlY forms the oxide scale. As a major constituent of the alloy, it provides a reservoir from which the alumina scale is constantly replenished. Replenishment, or film growth, is controlled by oxygen diffusing inwardly along alumina grain boundaries. The oxidation rate of MCrAlY is directly proportional to the formation rate of the alumina scale on its surface. Scale formation is attributed to the aluminum's activity and its diffusivity in the alloy. This activity is increased by the presence of chromium, which also enhances diffusion rate of the metal M. Adding chromium lowers the amount of aluminum needed to form and maintain the protective oxide film. If the aluminum content were increased instead of adding chromium, the MCrAlY alloy would show signs of brittleness.

FeCrAlY alloys exhibit high corrosion resistance and high sulfadation resistance. For optimum protection from hot corrosion, CoCrAlY alloys are preferred. "Hot corrosion" or high temperature corrosion is a form of corrosion that does not require the presence of a liquid electrolyte. An example of hot corrosion is oxidation. Nonetheless, CoCrAlYs are preferably limited to applications operating at temperatures below 927° C. NiCrAlYs can be used in a slightly higher temperature range than CoCrAlYs (up to 982° C.) and offer better oxidation protection than CoCrAlYs. The shortfalls of these two alloys can be overcome by substituting a small percentage of one for the other, or making either a NiCoCrAlY or CoNiCrAlY alloy.

In addition to combining M-base alloys, other metals known to improve the alloys' characteristics (i.e. silicon, hafnium, tantalum, and platinum) may be added. For example, silicon is a temperature suppressant and in small amounts is known to promote alumina scale adherence and, in some cases, form an oxide film of its own. Hafnium behaves in a manner similar to yttrium. After oxidizing to form hafnia needles, it locks the alumina scale in place. In some alloy systems, hafnium may be freely substituted for yttrium. Tantalum may be added to an MCrAlY alloy to improve the alloys' high-temperature capabilities and resistance to sulfidation and hot corrosion. Platinum may be added to an MCrAlY alloy to increase its oxidation and hot-corrosion properties for operating at temperatures up to 1093° C.

In the methods that employ catalysts for oxidative dehydrogenation of hydrocarbons to olefins, catalytic metals are typically dispersed throughout a ceramic oxide support. Ceramic oxides however, are known to have relatively low thermal conductivities. This poses a problem because of hot spots, in which the temperature is higher in localized regions than in the remaining part of the catalyst bed. Hot spots can form if catalyst loading or metal dispersion or resulting activity is uneven. These hot spots can give rise to secondary reactions, such as the total combustion of the starting material, or lead to the formation of undesired by-products, which can be separated from the reaction product only with great difficulty, if at all. Hot spot formation prevents attaining the desired process conditions, as well as leads to undesired reactions resulting in poor product yields, and in the worst case, in uncontrolled regimes i.e., runaway reactions and abrupt shutdowns.

A low gas flowrate is undesirable in especially short contact time reactors, because their processes are volume dependent (i.e. they operate at high gas space velocity). Accordingly, there is a continuing need for better, more economical processes and catalysts with good thermal and mechanical stability for the oxidative dehydrogenation of hydrocarbons, in which the catalyst retains a high level of activity and selectivity to olefins under conditions of high gas space velocity and elevated pressure.

SUMMARY OF THE INVENTION

In order to operate at very high flow rates, high pressure and using short contact time reactors, catalysts should be highly active, have excellent mechanical strength, resistance to rapid temperature fluctuations, thermal shocks and thermal stability at oxidative dehydrogenation reaction conditions.

The catalysts and methods of the present invention overcome some of the drawbacks of existing catalysts and processes for converting light hydrocarbons to olefins. The present ODS alloy-supported catalysts are expected to demonstrate greater thermal stability than ceramic oxide-supported catalysts and give comparable olefin yield to conventional oxidative dehydrogenation catalysts under conditions of high gas space velocity and elevated pressure. Another advantage provided by the preferred new catalysts and processes is that they are economically feasible for use under commercial-scale conditions.

The present invention provides a catalyst system for use in ODH that allows high conversion of the hydrocarbon feedstock at high gas hourly space velocities, while maintaining high selectivity of the process to the desired products. For the purposes of this disclosure, all listed metals are identified using the CAS naming convention.

In accordance with a preferred embodiment of the present invention, a catalyst for use in ODH processes includes a MCrAlY support. M is preferably a base metal, or combination of base metals. A base metal is herein defined as a non-Group VIII metal, with the exception of iron, cobalt and nickel. Suitable base metals include Group IB–VIIB metals, Group IIIA–VA metals, lanthanide metals, iron, cobalt and nickel. M preferably is iron, cobalt, nickel, indium, or manganese, and still more preferably iron, cobalt, or nickel. Additionally, the catalyst may optionally include a promoter such as a Group VIII metal. Suitable Group VIII promoters include Ru, Rh, Pd, Os, Ir, and Pt. The promoter is preferably deposited on the MCrAlY support.

Preferably, a millisecond contact time reactor, such as are known and described in the art, is used. By way of example only, operation of a millisecond contact time reactor is disclosed in detail in co-owned and co-pending U.S. Pat. No. 6,461,539 B1, filed Oct. 16, 2000 and entitled "Metal Carbide Catalysts and Process for Producing Synthesis Gas," which is incorporated herein by reference in its entirety.

In accordance with another preferred embodiment of the present invention, a method for the production of olefins includes contacting a preheated alkane and oxygen stream with an MCrAlY-supported catalyst, under conditions sufficient to initiate the oxidative dehydrogenation of the alkane (the preheat temperature preferably being between 25° C. and 800° C.), maintaining a contact time of the alkane with the catalyst for less than 200 milliseconds, and maintaining an oxidative dehydrogenation-favorable alkane:oxygen molar ratio.

These and other embodiments, features and advantages of the present invention will become apparent with reference to the following description.

DETAILED DESCRIPTION OF THE PREFERRED EMBODIMENTS

A new family of oxidative dehydrogenation catalysts having a MCrAlY support is described in the following representative examples. These catalysts are capable of catalytically converting $C_2$–$C_{10}$ hydrocarbons to olefins. They are preferably supported on any of various three-dimensional structures including, but not limited to, discs, foams, gauzes, honeycombs, spiral rolls of corrugated sheet, columnar or other configurations having longitudinal channels or passageways permitting high space velocities with a minimal pressure drop. Such configurations are known in the art and described in, for example, *Structured Catalysts and Reactors*, A. Cybulski and J. A. Moulijn (Eds.), Marcel Dekker, Inc., 1998, p. 599–615 (Ch. 21, X. Xu and J. A. Moulijn, "Transformation of a Structured Carrier into Structured Catalyst") incorporated herein by reference in pertinent part. The present support can also be provided in the form of a plurality of distinct or discrete structures or particulates. The terms "distinct" or "discrete" structures or units, as used herein, refer to nonmonolithic supports in the form of divided materials such as granules, beads, pills, pellets, cylinders, trilobes, extrudates, spheres or other rounded shapes, or other manufactured configurations. Alternatively, the particulate material may be in the form of irregularly shaped particles. Preferably at least a majority (i.e., >50%) of the particles or distinct structures have a maximum characteristic length (i.e., longest dimension) of less than six millimeters, preferably less than three millimeters, and most preferably less than 1.5 millimeters. The supports preferably have approximately 20 to 120 ppi (pores per linear inch), and more preferably 40–100 ppi.

The inventors have discovered that new MCrAlY-supported structures, when prepared as described in the following examples, are highly active oxidative dehydrogenation catalysts with sufficient mechanical strength to withstand high pressures and temperatures and permit a high flow rate of reactant and product gases when employed on-stream in a short contact time reactor for olefin production. The present MCrAlY structures may be catalytically active with and without the addition of further catalytic materials. Catalytic materials that can be added to the present MCrAlY structures include, but are not limited to, Group VIII metals. Without wishing to be restricted to a particular theory, the inventors believe that the high thermal conductivity of the MCrAlY support serves to minimize the occurrence of hot spots, which in turn, serves to limit secondary reactions (i.e. combustion), while maintaining sufficient crush strength. Crush strength, also known as mechanical strength, is herein defined as the load at which the support physically breaks.

Because MCrAlYs dissipate the heat formed during oxidative dehydrogenation effectively, secondary reactions are substantially prevented from equilibrating. This results in higher product selectivity, or a more selective catalyst. Additionally, by maintaining a lower temperature in the system, the catalytically active metals are less likely to volatilize in the reactor. In addition, MCrAlY performance is attributed to the alloys' ability to form a tenacious, protective scale that is formed during the high temperature oxidation of the component metals, which inhibits undesired interactions between the host surface and the reaction gases. The primary protective scale is aluminum oxide. Although other elements in the coating also can form oxides, they are not as protective as alumina.

Catalyst System

As discussed above, in accordance with a preferred embodiment, the present catalyst systems include a MCrAlY support. M is preferably a base metal, or combination of base metals. Suitable base metals include Group IB–VIIB metals, Group IIIA–VA metals, Lanthanide metals, iron, cobalt and nickel.

One preferred ODS alloy for use as a catalyst support with the present invention consists of, by weight, 15 to 25% chromium (Cr), 3 to 6% aluminum (Al), 0.1 to 1.0% $Y_2O_3$, 0.1 to 1.0% titanium (Ti), and the balance iron (Fe). These alloys are designated Fe-base ODS alloys, or FeCrAlYs, and are readily commercially available.

Other preferred ODS alloys include Ni-base, Co-base, Mn-base and In-base alloys. Fe-base or Ni-base or Co-base alloys that do not contain an oxide dispersion but contain Cr and Al can also be satisfactorily used as catalyst supports in the present invention.

The present catalyst support is preferably pretreated by heating in air or oxygen at 800 to 1200° C., preferably at about 850 to about 1000° C., and more preferably at about 900° C., for from 5 to 100 hours, preferably from 5 to 20 hours, and even more preferably for about 10 hours to form a thin, tightly adhering oxide surface layer that protects the underlying support alloy from further oxidation during high temperature use. The surface layer also functions as a diffusion barrier to the supported catalyst metal (e.g. Ru, Rh, Pd, Os, Ir, and Pt, and combinations thereof), thus preventing alloying of the catalyst metal with the alloy of the catalyst support. The protective surface layer is preferably composed predominantly of alpha-alumina, but may also contain a small amount of yttrium oxide.

After pretreatment, the catalyst supports are coated with active metal components such as Group VIII promoters, including Ru, Rh, Pd, Os, Ir, Pd, and Pt, and any combinations thereof. In a preferred embodiment, the promoter is selected from the group consisting of Pt and Pd. The coating may be achieved by any of a variety of methods known in the art, such as physical vapor deposition, chemical vapor deposition, electrolysis metal deposition, electroplating, melt impregnation, and incipient wetness impregnation, followed by one or more calcination steps (heating in air or oxygen), and then optionally a reduction, preferably with hydrogen.

One way of preparing the support and applying the promoter may be preferred over another, depending for example on the desired catalyst support configuration. Those skilled in the art are readily able to select the most suitable techniques for a given set of requirements. For example, another embodiment of this invention uses a front-loaded promoter on the ODS-supported catalyst bed. By way of example only, this can be achieved by placing a thin layer of promoter on top of the catalytic bed, or by placing a disc preloaded with one or more promoters such as preferably platinum or palladium upstream of the ODS-based catalytic bed. The disc could comprise an ODS alloy, a MCrAlY that could be the same as or different from that used in the catalytic bed, a refractory material, a ceramic oxide, a metal oxide or combination thereof. Preferably the promoter-preloaded disc comprises a refractory material, such as aluminum oxide ($Al_2O_3$). When the promoter is front-loaded on the ODS alloy catalytic bed, the MCrAlY-based support preferably comprises a Lanthanide metal.

Preferably, a millisecond contact time reactor is used. Use of a millisecond contact time reactor for the commercial scale conversion of light alkanes to corresponding alkenes will reduce capital investment and increase alkene production significantly. It has been discovered that an ethylene yield of 55% or higher in a single pass through the catalyst bed is achievable. This technology has the potential to achieve yields above that of the conventional technology at a much lower cost. In some embodiments, steam may be used. There is minimal coking in the present process and therefore little unit down time and loss of valuable hydrocarbon feedstock. The present novel catalysts improve the selectivity of the process to the desired alkene In some embodiments, ODH is carried out using the hydrocarbon feed mixed with an appropriate oxidant and possibly steam. Appropriate oxidants may include, but are not limited to, air, oxygen-enriched air, $I_2$, $O_2$, $N_2O$, $CO_2$ and $SO_2$. Use of the oxidant prevents coke deposition and aids in maintaining the reaction. Steam, on the other hand, may be used to activate the catalyst, remove coke from the catalyst, or serve as a diluent for temperature control.

Without further elaboration, it is believed that one skilled in the art can, using the description herein, utilize the present invention to its fullest extent. The following embodiments are to be construed as illustrative, and not as limiting the disclosure in any way.

EXAMPLES

In the following examples, commercial 60-ppi FeCrAlY foam is used as catalyst support to illustrate the catalyst of the invention and a preferred method of its preparation. Those skilled in the art will appreciate that many other configurations of catalyst support are possible without departing from the scope of the present invention by either using another commercially available MCrAlY alloy or by producing such alloy by using methods such as those described in the prior art. An example of one such method is disclosed in U.S. Pat. No. 6,410,159.

Preparation of the Catalyst

Catalyst synthesis conditions: All catalysts were supported on ½"D×1"L, 60 ppi FeCrAlY foam support. The approximate composition of this material is 73% Fe-20% Cr-5% Al-2% by weight. The FeCrAlY support was pretreated at 1050° C. for 10 hrs in air before loading metals with standard impregnation procedures. Following the impregnation of metal solutions, the supports were dried at 80° C. in vacuum for 1 hour and calcined at 500° C. for 3 hours in air. Then the materials were subjected to reduction by 50% hydrogen ($N_2$ as balance) at 500° C. for 3 hours.

The pretreated foam was then coated with a promoter. The promoter was preferably either Pt or Pd. For platinum and palladium, the metal loading is preferably between about 0.01 and about 5 weight %, more preferably between about 0.1 and about 1.0 weight %. The support may be prepared in any suitable manner. Likewise, the promoter may be applied in any suitable manner. In some instances, the desired catalyst support configuration will dictate the preferred techniques.

To prepare Pt disks, the disks (½"D×1/32"T) were cut from $Al_2O_3$ fiber mats purchased from Cotronics. The disks were then impregnated with Pt solutions and dried in vacuum at 80° C. for 1 hour. No high temperature treatment is necessary, although it may be used.

Other catalyst support alloys may of course be used without departing from the scope of the invention, provided that a similar protective layer of oxide scale is formed upon pretreatment as described herein. Those skilled in the art are readily able to select the most suitable techniques for a given set of requirements.

Experiment Setup

Ethane and oxygen came from gas cylinders and were controlled by gas flow controllers. They were mixed through a static mixer; then the mixture was fed to the reactor. The reactor was a 9/16" inside diameter quartz tubing and operated at a residence time less than 200 milliseconds. An electric heater was located at the upstream of a catalyst bed and used to pre-heat the reactor feed at a temperature range of 100° C.–600° C. A cooler was located at the downstream of a catalyst bed and used to rapidly cool product stream down to below 35° C. to condense most of the water vapor. A small part of the product gas stream was sent to a gas chromatograph for composition analysis.

Testing Procedure

The catalysts were packed between two blank ceramic foams in a reactor. The bottom foam was used as a catalyst bed support while the top foam was used as a shield. The reactor feed was a mixture of ethane, oxygen and nitrogen. The feed flow rates were measured at normal temperature and pressure (15.6° C., 1 atm). The feed was pre-heated to help the catalyst bed light off. When the catalyst bed lit off, the feed temperature at the top of the foam shield was controlled at a desired value between 100° and 600° C. The products from the reactor included ethylene, acetylene, CO, $CO_2$, $H_2$, water vapor, and other hydrocarbons. The operating pressure was between 1.2 and 1.8 atm.

Another embodiment of this invention uses a front-loaded promoter on the ODS-supported catalyst bed. By way of example, this can be achieved by placing a thin layer of promoter on top of the catalytic bed, or by placing a disc preloaded with one or more promoters, such as preferably platinum or palladium, upstream of the ODS-based catalytic bed. The disc could comprise an ODS alloy, a MCrAlY that could be the same as or different than that used in the catalytic bed, a refractory material, a ceramic oxide, a metal oxide or combination thereof. Preferably the promoter-preloaded disc comprises a refractory material, such as aluminum oxide ($Al_2O_3$). When the promoter is front-loaded on the ODS alloy catalytic bed, the MCrAlY-based support preferably comprises a lanthanide metal.

Test Results

For test conditions using an ethane: O2 ratio of 2.0 and a preheat temperature of 300° C., the results are given below. Each catalyst was promoted with an $Al_2O_3$ fiber disk (Cotronics) containing 5 μmole (or 1 mg) Pt.

TABLE 1

Flow rate = 3.0 SLPM

| Catalyst | % Ethane Conv. | % Oxygen Conv. | % Ethylene C Sel. | % Ethylene yield |
|---|---|---|---|---|
| 0.1 Pt/FeCrAlY | 73 | 96 | 70 | 51 |
| 1 Pt/FeCrAlY | 76 | 97 | 69 | 52 |
| 0.1 Pd/FeCrAlY | 76 | 98 | 68 | 52 |

Additional tests were performed using catalyst samples made according to another preferred embodiment of the invention. Lanthanide metals such as Pr, Tb, and Sm, were deposited via incipient wetness impregnation on the pretreated Porvair ½"D×1"H 60-ppi FeCrAlY foam. Platinum was pre-loaded on $Al_2O_3$ ½'"D mats from Cotronics, and placed upstream (i.e., on top) of LnFeCrAlY-based alloy foam. The results are given in Table 2 below.

TABLE 2

Flow rate = 5.0 SLPM

| Catalyst | % Ethane Conv. | % Oxygen Conv. | % Ethylene C Sel. | % Ethylene yield |
|---|---|---|---|---|
| 6.2% Pr/FeCrAlY | 87 | 100 | 68 | 60 |
| 8.7% Tb/FeCrAlY | 85 | 100 | 68 | 57 |
| 6.6% Sm/FeCrAlY | 84 | 100 | 69 | 57 |

Process Conditions

Any suitable reaction regime is applied in order to contact the reactants with the catalyst. One suitable regime is a fixed bed reaction regime, in which the catalyst is retained within a reaction zone in a fixed arrangement. Catalysts may be employed in the fixed bed regime, retained using fixed bed reaction techniques well known in the art. Preferably a millisecond contact time reactor is employed, such as are known in the art.

Accordingly, a feed stream comprising a hydrocarbon feedstock and an oxygen-containing gas is contacted with one of the above-described catalysts in a reaction zone maintained at conversion-promoting conditions effective to produce an effluent stream comprising alkenes. The hydrocarbon feedstock may be any gaseous hydrocarbon having a low boiling point, such as ethane, natural gas, associated gas, or other sources of light hydrocarbons having from 2 to 10 carbon atoms. In addition, hydrocarbon feeds including naphtha and similar feeds may be employed. The hydrocarbon feedstock may be a gas arising from naturally occurring reserves of ethane. Preferably, the feed comprises at least 50% by volume alkanes (<$C_{10}$).

The hydrocarbon feedstock is contacted with the catalyst as a gaseous phase mixture with an oxygen-containing gas, which is preferably pure oxygen, but may alternatively be air or $O_2$-enriched air. The oxygen-containing gas may also comprise steam and/or methane in addition to oxygen. Preferably, the composition of the reactant mixture is such that the atomic oxygen-to-carbon ratio is between about 0.05:1 and about 5:1. In some embodiments, the reactant mixture may also comprise steam. Steam may be used to activate the catalyst, remove coke from the catalyst, or serve as a diluent for temperature control. The ratio of steam to carbon by weight, when steam is added, may preferably range from about 0 to about 1. Alternatively, the hydrocarbon feedstock is contacted with the catalyst as a mixture with a gas comprising steam and/or methane.

The process is operated from sub to super atmospheric pressures, the latter being preferred. The pressures may be from about 80 kPa to about 32,500 kPa, more preferably from about 130 kPa to about 10,000 kPa, and still more preferably from about 200 kPa to about 3,500 kPa. The preheat temperature of the present invention is preferably between about 25° C. to about 800° C., more preferably between about 150° C. and about 700° C., more preferably between about 150° C. and about 600° C., and still more preferably between about 150° C. and about 500° C. The hydrocarbon feedstock and the oxygen-containing gas are preferably pre-heated before contact with the catalyst. The hydrocarbon feedstock and the oxygen-containing gas are preferably pre-mixed before contact with the catalyst.

The hydrocarbon feedstock and the oxygen-containing gas are passed over the catalyst at any of a variety of space velocities. Gas hourly space velocities (GHSV) for the present process, stated as volume of feed gas at standard conditions per catalyst bed volume per hour, are preferably from about 20,000 to at least about 100,000,000 $hr^{-1}$, and more preferably from about 50,000 to about 1,000,000 $hr^{-1}$. The present catalyst is preferably employed in a millisecond contact time reactor. The process preferably includes maintaining a catalyst residence time of no more than 200 milliseconds for the reactant gas mixture. Residence time is inversely proportional to space velocity, and high space velocity indicates low residence time on the catalyst. An effluent stream of product gases, including alkenes, alkynes, CO, $CO_2$, $H_2$, $H_2O$, and unconverted reactant gases emerge from the reactor.

In some embodiments, unconverted alkanes may be separated from the effluent stream of product gases and recycled back into the feed.

While the preferred embodiments of the invention have been shown and described, modifications thereof can be made by one skilled in the art without departing from the spirit and teachings of the invention. The embodiments described herein are exemplary only, and are not intended to be limiting. Many variations and modifications of the invention disclosed herein are possible and are within the scope of the invention. For example, the present invention may be incorporated into a gas to liquids plant (GTL) or may stand alone. Accordingly, the scope of protection is not limited by the description set out above, but is only limited by the claims which follow, that scope including all equivalents of the subject matter of the claims. The disclosures of all patents and publications cited herein are incorporated by reference in their entireties.

What is claimed is:

1. A method for the production of olefins comprising:
   a) heating a feed stream comprising at least an alkane and an oxidant to a temperature of between approximately 25° C. and 800° C.;
   b) contacting the feed stream with a catalyst comprising an MCrAlY structure, wherein M is a base metal, or combination of base metals; and
   c) maintaining a contact time of the feed stream with the catalyst of less than 200 milliseconds under conditions sufficient to achieve oxidative dehydrogenation of the alkane.

2. The method of claim 1 wherein the catalyst further includes a Group VIII promoter metal coating.

3. The method of claim 1 wherein the oxidant comprises a molecular oxygen-containing gas.

4. The method of claim 3 wherein the molecular oxygen-containing gas is air, oxygen-enriched air, or pure oxygen.

5. The method of claim 1 wherein the alkane comprises at least one paraffin with a carbon number between 2 and 10.

6. The method of claim 1 wherein M comprises a metal selected from the group consisting of Group IB–VIIB metals, Group III–VA metals, lanthanide metals, iron, cobalt, nickel, and combinations thereof.

7. The method of claim 6 wherein M comprises a metal selected from the group consisting Tb, Sm, Pr, Fe, Ni, Co, and combinations thereof.

8. The method of claim 1 wherein the feed stream comprises gaseous hydrocarbons.

9. The method of claim 8 wherein the catalyst further includes a Group VIII promoter metal coating.

10. The method of claim 9 wherein the oxidant is comprises a molecular oxygen-containing gas.

11. The method of claim 10 wherein the molecular oxygen-containing gas is air, oxygen-enriched air, or pure oxygen.

12. The method of claim 8 wherein the alkane comprises at least one paraffin with a carbon number between 2 and 10.

13. The method of claim 8 wherein M comprises a metal selected from the group consisting of Group IB–VIIB metals, Group IIIA–VA metals, lanthanide metals, iron, cobalt, nickel, and combinations thereof.

14. The method of claim 13 wherein M comprises a metal selected from the group consisting Tb, Sm, Pr, Fe, Ni, Co, and combinations thereof.

15. A method for the production of olefins comprising:
   a) heating a feed stream comprising at least an alkane and an oxidant to a temperature of between approximately 25° C. and 800° C.; and
   b) contacting the feed stream with a catalyst comprising an MCrAlY structure, wherein M is a base metal, or combination of base metals.

16. The method of claim 1 wherein the catalyst further includes a Group VIII promoter metal.

17. The method of claim 1 wherein the oxidant comprises a molecular oxygen-containing gas.

18. The method of claim 3 wherein the molecular oxygen-containing gas is air, oxygen-enriched air, or pure oxygen.

19. The method of claim 1 wherein the alkane comprises at least one paraffin with a carbon number between 2 and 10.

20. The method of claim 1 wherein M comprises a metal selected from the group consisting of Group IB–VIIB metals, Group IIIA–VA metals, lanthanide metals, iron, cobalt, nickel, and combinations thereof.

21. The method of claim 6 wherein M comprises a metal selected from the group consisting Tb, Sm, Pr, Fe, Ni, Co, and combinations thereof.

* * * * *